United States Patent [19]

Neumann

[11] 4,260,894
[45] Apr. 7, 1981

[54] OPTIMUM DOSE TOMOGRAPHY SCANNING SYSTEM

[75] Inventor: Leopold Neumann, Lexington, Mass.

[73] Assignee: Siemens Aktiengesellschaft, Berlin & Munich, Fed. Rep. of Germany

[21] Appl. No.: 965,152

[22] Filed: Nov. 30, 1978

[51] Int. Cl.³ ............................................. G03B 41/16
[52] U.S. Cl. .................................. 250/445 T; 250/413
[58] Field of Search .................... 250/445 T, 402, 413

[56] References Cited

U.S. PATENT DOCUMENTS

| 4,032,784 | 6/1977 | Rich | 250/445 T |
| 4,051,377 | 9/1977 | Kemner | 250/445 T |

FOREIGN PATENT DOCUMENTS 1283915  8/1972  United Kingdom ................ 250/445 T Primary Examiner—Craig E. Church
Attorney, Agent, or Firm—Hill, Van Santen, Steadman, Chiara & Simpson

[57] ABSTRACT

A tomography scanning system in which the intensity of radiation for each exposure is adjusted to obtain at the system detectors a minimum signal which results in a desired minimum signal-to-noise ratio to provide an image of acceptable quality with minimum radiation dosage to a patient.

1 Claim, 4 Drawing Figures

FIG. 1
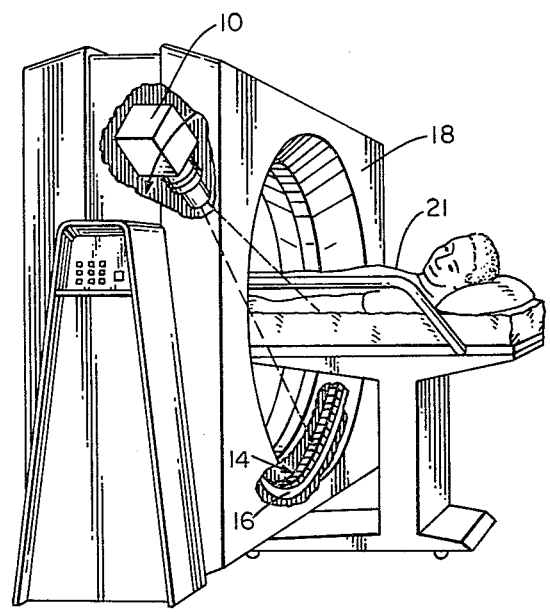
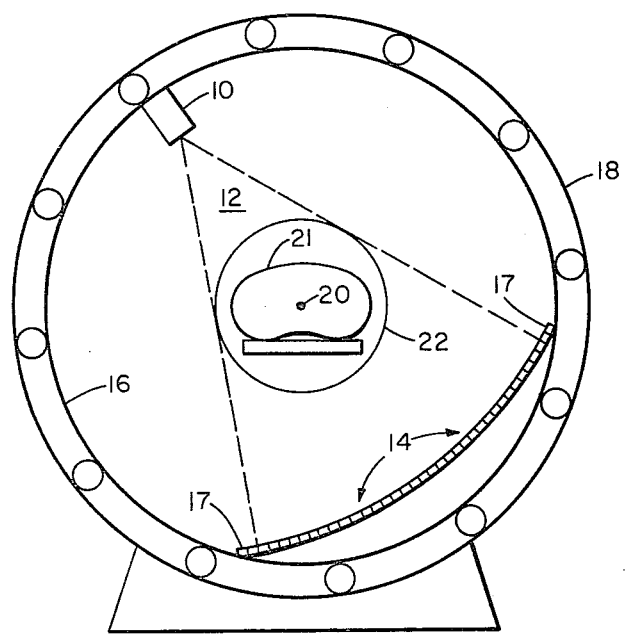
FIG. 1A

OPTIMUM DOSE TOMOGRAPHY SCANNING SYSTEM

CROSS REFERENCE TO RELATED APPLICATION

Pursuant to 37 CFR 1.79, reference is made to a divisional application directed particularly to the subject matter of FIG. 3 of the present application, and which is being filed on or about Nov. 6, 1980.

FIELD OF THE INVENTION

This invention relates to x-ray systems and in particular to x-ray systems wherein a plurality of sequential exposures are taken, such as a computerized tomography scanning system.

BACKGROUND OF THE INVENTION

In designing x-ray systems for producing images of human subjects, one of the primary considerations is reducing the exposure to radiation which is experienced by the patient. In computerized tomography x-ray scanning systems, there is generally an x-ray source and an array of radiation detectors which are both movable relative to the body being imaged. As the x-ray source and detector move relative to the patient, a large number of x-ray images are taken, and the data from these images is processed to provide a representation of the cross-sectional density of the subject.

In known tomography scanners, the radiation level provided by the x-ray source for each exposure is selected prior to the beginning of the x-ray scan. The particular exposure value chosen is dependent on the patient's size and on the section of the body being examined, and the exposure is not changed as the scanner rotates about the patient. Since attenuation through the body is significantly different for views taken from different angles, the use of a single preselected exposure value results in the patient being exposed to more radiation than is needed for exposures at most angles. Additionally, in conventional systems, the exposure settings are determined using tables based on typical size and weight characteristics of patients, and these tables do not always produce an optimum exposure selection for actual patients.

SUMMARY OF THE INVENTION

The present invention provides a tomographic scanning system in which the intensity of radiation for each exposure is adjusted to obtain at the detectors a preset minimum signal which results in a desired minimum signal-to-noise ratio. By choosing the signal-to-noise ratio to be the minimum necessary to produce an image of acceptable quality, the radiation dose to the patient is minimized.

In a preferred embodiment adapted for use with a pulsed x-ray system, the output signal from one or more detectors is monitored; and when all the integrals of the output signals from these detectors reach a predetermined threshold, the x-ray pulse is terminated. Of the radiation passing through a patient, radiation passing through the center of the patient normally is attenuated by the maximum amount. By monitoring signals from centrally-located detectors receiving this radiation, once the signals from these detectors reach a predetermined threshold, no further exposure is necessary to produce an image having the desired quality.

In an alternate embodiment, applicable to both pulsed and continuous x-ray systems, selected detector output signals are compared with a desired minimum value following each exposure. The next exposure is varied in accordance with the results of this comparison. The projection angle between successive exposures changes by a small amount, on the order of a degree or less, and the attenuation of x-ray energy between successive views will vary only slightly. Thus, determining the proper exposure for the next projection based on the attenuation determined from the last projection will produce an exposure which, for practical purposes, is substantially equal to the optimum exposure.

DESCRIPTION OF THE DRAWINGS

These and other advantages of the present invention will be more fully understood from the following detailed description of the invention taken in conjunction with the accompanying drawings in which:

FIG. 1 is a pictorial view of a typical tomographic scanning system in which the invention is employed;

FIG. 1A is an elevation view of a typical tomographic scanning system;

DETAILED DESCRIPTION OF THE INVENTION

Figure 2:
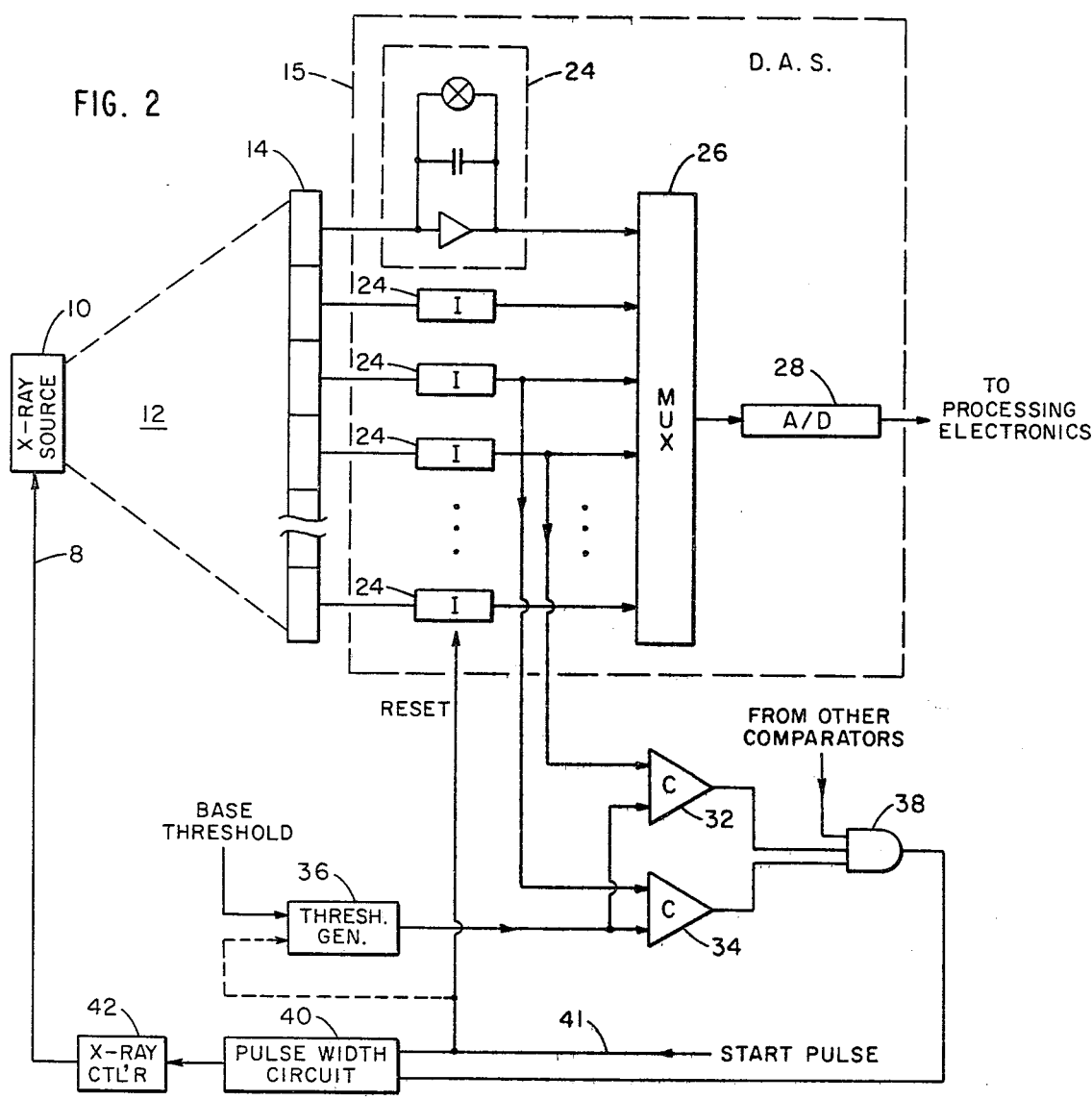
FIG. 2 is a block diagram of one embodiment of the present invention adapted for use with pulsed x-ray scanner systems.

Referring to FIGS. 1 and 1A, there is shown a fan-beam-type of tomographic scanning system in which the invention is employed. It will be appreciated that the present invention is equally applicable to tomographic scanners other than fan-beam type scanners, including parallel beam scanners, detector source type scanners and systems employing radiation other than x-rays. The embodiment described is for exemplary purposes only and is not to be construed as a limitation upon the present invention.

Typically, a tomography system includes an x-ray tube 10 or other source of radiation which projects a beam of radiation, such as a fan-shaped beam 12, which passes through a patient 21 being scanned and impinges upon a detector array 14 having a plurality of detectors which produce output signals proportional to the intensity of received radiation. The x-ray source 10 and detector array 14 are mounted on an inner ring 16 of a gantry structure so that the source 10 and detector array 14 are maintained in a fixed relationship to one another. The inner ring 16 is rotatably mounted within an outer ring 18, such as by rollers 19, so that the inner ring 16 can be rotated within stationary ring 18, thereby revolving x-ray source 10 and detector array 14 about an axis 20 at the center of ring 16 and perpendicular to the plane of fan-beam 12.

As the x-ray source 10 and detector array 14 are rotated about the patient 21, a plurality of x-ray exposures, called projections, are taken of the patient from different angles. This causes the radiation beam 12 to illuminate a circular area, shown by line 22 in FIG. 1A, as the inner ring 16 of the gantry is rotated through one complete revolution, called a scan. The patient 21 being scanned is placed within circular area 22 and x-rays passing through the patient impinge upon the detector array 14. Typically, detector array 14 will include monitor detectors 17 located at one or both ends of the detector array and which receive unattenuated x-rays passing outside of circular area 22. Thus, the x-rays impinging upon the monitor detectors 17 provide an indication of the x-ray intensity from x-ray source 10 for each projection, without attenuation from passage through a patient.

The angle of illumination by x-ray source 10 of area 22 with respect to the stationary body 21 is called the projection angle. By taking data from detector array 14 at a plurality of different projection angles, a tomographic scan of a patient or other object placed in area 22 may be taken; and by suitably processing the data from the detector array, a picture may be formed representative of the density of a patient in the cross-sectional area lying in the plane of fan-beam 12. One typical tomographic system with which the present invention may be used is shown and described in U.S. patent application Ser. No. 824,632, filed Aug. 15, 1977, entitled "Tomography Signal Processing System," now U.S. Pat. No. 4,135,247 issued Jan. 16, 1979.

One area of particular concern in tomographic scanning systems is minimizing the radiation exposure to which the patient is subjected. Due to the fact that a tomographic scan requires a large number of projections, typically numbered in the hundreds, this problem is more critical with tomography scanners than with conventional x-ray systems.

It can be seen that as the x-ray source 10 and detector array 14 rotate about patient 21, the body thickness, and hence the x-ray beam attenuation, will vary over a wide range. For example, referring to FIG. 1A, when x-ray source 10 is directly above the patient 21, the thickness of the body section through which the x-rays pass and by which the x-rays are attenuated is much smaller than when x-ray source 10 and detector array 14 are oriented horizontally, such that the x-rays must pass from side to side through the body of patient 21.

In conventional systems having a fixed exposure, the x-ray intensity is set to produce acceptable levels of radiation at detector array 14 for the highest degree of attenuation experienced by the beam 12. In FIG. 1A, this would occur when x-ray source 10 and detector array 14 are horizontally oriented. For other projection angles, the attenuation of the x-ray beam by the patient 21 will be less, and the radiation exposure to the patient for these other angles is greater than necessary.

In accordance with this invention, adjustment is appropriately made of the x-ray exposure from x-ray source 10 to an optimum value for each projection during a scan, such that the radiation exposure of patient 21 is reduced without degradation of picture quality. Referring to FIG. 2, there is shown one preferred embodiment of the present invention which is particularly adapted for use with x-ray scanners in which the exposure is controlled by varying the duration, or pulse width, of the x-ray emission from x-ray source 10. This circuitry operates in the following manner. In response to a pulse provided on line 8 to x-ray source 10, the source 10 provides a pulsed beam of radiation 12 which impinges upon the detector array 14 and which has a duration substantially equal to the width of the pulse on line 8. Although not shown in FIG. 2, it is to be understood that a patient or other body being scanned is within the beam 12 of x-rays.

Detector array 14 includes a plurality of individual detectors responsive to x-radiation which provide output signals representative of the level of radiation received. The signals from the detector array 14 are applied to a data acquisition system (DAS), shown within box 15, which converts the low-level analog signals from the detectors to digitized signals which are applied to the tomographic processor which produces the final image. Typically, the output from each detector in detector array 14 is applied to a respective reset integrator 24. Integrators 24 are reset prior to each x-ray exposure. The output signal from each of the detectors 14 is integrated by the respective integrator 24 during the x-ray exposure to produce an output signal representative of the received x-ray intensity. The output signals from each of the integrators 24 are applied to an analog multiplexer (MUX) 26. The multiplexer 26 is operative to sequentially apply each of the integrator output signals to an analog-to-digital converter 28 which provides a digital representation of each of the integrator output signals. These digitized signals are then processed by well-known computerized tomography processors to produce a final image representative of the cross-sectional area being scanned.

The exposure control of the present invention is performed in the following manner. The output signals from one or more of the integrators 24 are applied to respective comparators which determine when the corresponding integrator output signal has exceeded a preselected threshold. In FIG. 2, the output from two integrators 24 are applied via lines 30 to first inputs of comparators 32 and 34. The second inputs to comparators 32 and 34 are provided by a threshold generator 36. Generally, the output signal from integrators associated with centrally located detectors are used to determine the exposure, since these detectors will normally receive the lowest level signals. The threshold level from threshold generator 36 is selected to correspond with the minimum signal from integrators 24 which will provide the desired signal-to-noise ratio. The output from comparators 32 and 34 are applied to an AND gate 38. In response to a high level from both comparators 32 and 34, indicating that the corresponding integrator output signals on lines 30 have both exceeded the threshold level set by threshold generator 36, the output from AND gate 38 goes high, indicating that the x-ray exposure should be ended. While the circuitry shown in FIG. 2 has only two signals from integrators 24 applied to two comparators, it will be appreciated that a greater or lesser number of integrator output signals may be monitored to determine the exposure.

A pulse-width circuit 40 receives a "start" pulse on line 41 which initiates each x-ray exposure during each projection. The "start" pulse may also be used to reset integrators 24. The output signal from AND gate 38, indicating when the exposure should be ended, is also applied to pulse-width circuit 40. In response to a start pulse, pulse-width circuit 40 provides a signal to the x-ray controller 42 which causes x-ray source 10 to begin an exposure. When the desired exposure level has been reached, AND gate 38 provides a signal representative thereof which is applied to pulse-width circuit 40. In response to this signal, pulse-width circuit 40 causes x-ray controller 42 to turn off x-ray source 10, ending the exposure. In this manner, the radiation to which a patient is exposed may be kept to a minimum, while still providing acceptable quality in the final image.

A certain interval of time elapses following a control signal to turn off source 10 before radiation from source 10 is actually discontinued. To compensate for such time delay, it is often desirable to provide a time variable threshold in threshold generator 36 which is lowered by an amount determined to take into account the time delay and thereby to provide termination of radiation from source 10 at the intended time. The threshold generator 36 can be implemented by well-known circuit techniques to provide a threshold characteristic to accommodate the delay characteristics of the x-ray source and associated control electronics.

Figure 3:
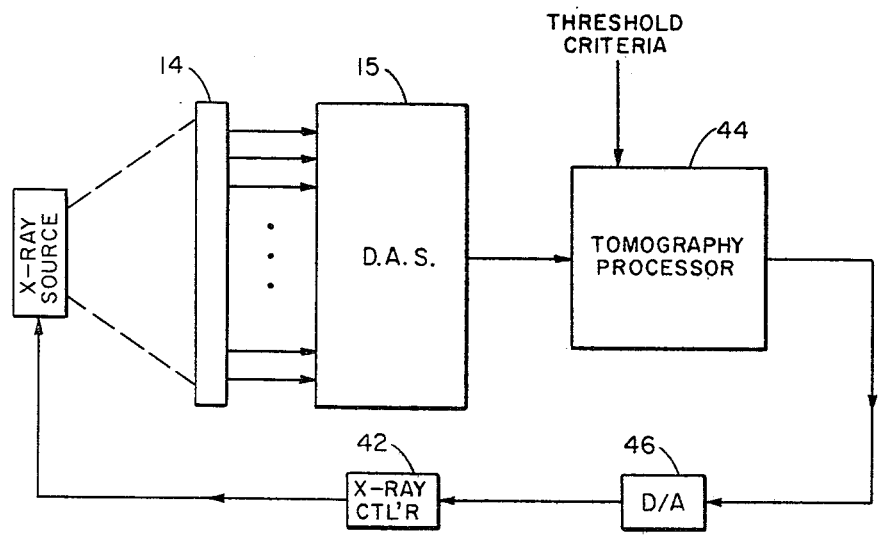
FIG. 3 is a block diagram of an alternate embodiment of the present invention.

An alternate embodiment is shown in FIG. 3 wherein the magnitude of exposure is determined in accordance with the level of radiation received by the detector array during the previous exposure. Referring to FIG. 3, an x-ray source 10 provides a beam of radiation 12 which impinges upon detector array 14, as described above. The output signals from the detectors in array 14 are applied to data acquisition system 15, which can be similar to that shown in FIG. 2, and the output data from which is applied to a tomographic processor 44 which is operative to produce a final image representing the cross-sectional area being scanned. At the conclusion of each projection or exposure, the magnitude of the next exposure is determined in accordance with the level of radiation received by detector array 14 during the previous exposure. The exposure intensity is determined by monitoring of the output signals from one or more of the detectors of array 14 to provide a minimum signal level which is greater by a predetermined amount than the known noise level, thereby to maintain an intended signal-to-noise ratio.

Determination of the intensity of the next exposure can be accomplished by means of processor 44 which receives data representing the threshold criteria to provide the intended signal-to-noise ratio. The processor 44 provides, after each projection, a digital signal representative of the radiation level for the next projection, and this digital signal is applied to a digital-to-analog converter 46, the output of which is an analog signal applied to x-ray controller 42. The controller 42 is coupled to x-ray source 10 and is operative to cause the generation of a desired exposure by source 10 during the next projection. The processor 44 is typically a computer-based processor wherein the desired control functions are specified by appropriate software routines. Alternatively, exposure determination can also be provided by special purpose analog or digital circuits associated with data acquisition system 15 or otherwise provided in the tomography system. Calculation of exposure level for each projection based upon the level of radiation from the prior projection results in only a small non-appreciable error, since the movement between projections of x-ray source 10 and detector array 14 is small, generally a degree or less, and thus the level of received radiation does not vary widely from one projection to the next.

The controller 42 will typically vary one or more parameters of the x-ray source 10 in order to provide the desired exposure. In a continuous system, the parameter which may best be varied is the x-ray tube current; while in a pulsed x-ray system, the pulse width is most easily varied. However, it should be clear that other parameters may also be varied to give the desired exposure. The determination of the next exposure level may be based on all of the detector outputs or may be based on a selection of outputs, which typically would include detectors near the center of detector array 14 which normally receive the minimum signal.

There has been described herein a novel system for providing control of the x-ray exposure in a tomographic scanner to minimize the radiation dose received by a patient while maintaining a desired minimum image quality. It will be appreciated that modifications to the preferred embodiments of the invention described herein may be made by those of ordinary skill in the art without departing from the intended scope of the invention. Therefore, the invention is not to be limited, except as indicated in the appended claims.

What is claimed is:

1. In a tomography system for producing a cross-sectional image of a body,
    a radiation source providing a fan-shaped beam of radiation,
    a detector array including a series of detectors arranged to simultaneously receive radiation from said source after transmission through a body layer to be examined, each detector producing an output signal representative of the level of received radiation,
    a series of resettable integrators each connected with a respective one of said series of detectors and operable during a radiation exposure cycle to integrate the respective output signal therefrom and each having an output to supply an integrated output signal representing the time integral of the radiation received by such detector during a radiation exposure cycle,
    start means for supplying a start signal for starting each of a series of radiation exposure cycles and for resetting the resettable integrators at the start of each radiation exposure cycle,
    control means, connected to said radiation source and to said start means, and responsive to said start signal, for causing said radiation source to emit a fan-shaped beam of radiation upon the occurrence of the start signal,
    threshold setting means for setting a threshold value and for producing a threshold value signal representative thereof,
    monitoring means connected with the outputs of a plurality of said resettable integrators for monitoring the integrated output signals respectively supplied by said plurality of resettable integrators, said monitoring means comprising a plurality of comparators each operative to compare two input signals and produce a comparator output signal representative of the relative magnitudes thereof, each comparator receiving as one input thereto a respective one of the integrated output signals, and as the other input thereto receiving the threshold value signal from said threshold setting means, and
    gate means responsive to said comparator output signals for producing a gating output signal only when all of the integrated output signals have exceeded the threshold value as set by said threshold setting means, and
    means for coupling said gating output signal to said control means,
    said control means being responsive to said gating output signal to cause the radiation source to cease producing said fan-shaped beam of radiation, upon exceedance of the threshold value by the integrated output signals of all of said plurality of resettable integrators connected with said monitoring means.

* * * * *